United States Patent [19]

Wohlers et al.

[11] Patent Number: 5,403,264
[45] Date of Patent: Apr. 4, 1995

[54] ENDOSCOPIC CLOSURE INSPECTION DEVICE

[75] Inventors: Udo Wohlers, Hamburg; Jean-Pierre Kinet, Hensted-Ulzburg, both of Germany; Dale Schulze, Lebanon, Ohio; Kirsten Huss, Ahrensburg, Germany

[73] Assignee: Ethicon, Inc., Somerville, N.J.

[21] Appl. No.: 114,576

[22] Filed: Aug. 31, 1993

[30] Foreign Application Priority Data

Sep. 4, 1992 [DE] Germany ............... 42 29 873.3

[51] Int. Cl.6 ............................................. A61B 19/00
[52] U.S. Cl. .................................. 600/32; 128/4; 604/27; 604/93; 604/174; 604/278
[58] Field of Search ............ 604/27, 93, 264, 278; 606/108, 191; 600/29, 32; 128/4, DIG. 26

[56] References Cited

U.S. PATENT DOCUMENTS

| | | | |
|---|---|---|---|
| 3,253,594 | 5/1966 | Matthews et al. | 128/348 |
| 4,217,664 | 8/1980 | Faso | 600/32 |
| 4,258,704 | 3/1981 | Hill | 600/32 |
| 4,338,937 | 7/1982 | Lerman | 600/32 |
| 4,608,965 | 9/1986 | Anspach, Jr. et al. | 128/4 |
| 4,686,965 | 8/1987 | Bonnet et al. | 128/4 |
| 4,915,694 | 4/1990 | Yamamoto et al. | 604/180 |
| 5,073,169 | 12/1991 | Raiken | 604/174 X |
| 5,234,455 | 8/1993 | Millhollan | 606/191 |
| 5,290,249 | 3/1994 | Foster et al. | 604/174 |

FOREIGN PATENT DOCUMENTS 9308729  5/1993  WIPO ............... 128/4

Primary Examiner—Richard J. Apley
Assistant Examiner—Beverly A. Meindl
Attorney, Agent, or Firm—Paul A. Coletti

[57] ABSTRACT

An endoscopic inspection closure is described which has a guide device preventing the puncture incision created by a trocar obturator and cannula from closing and a closure device which fits within the guide device. The closure device is removable after the initial endoscopic operation, for observation of healing and introduction of endoscopic surgical instruments.

12 Claims, 3 Drawing Sheets

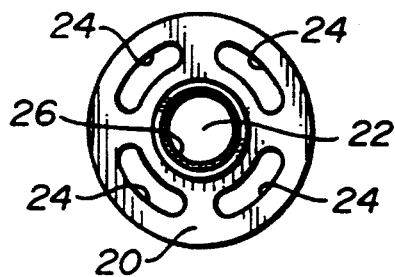
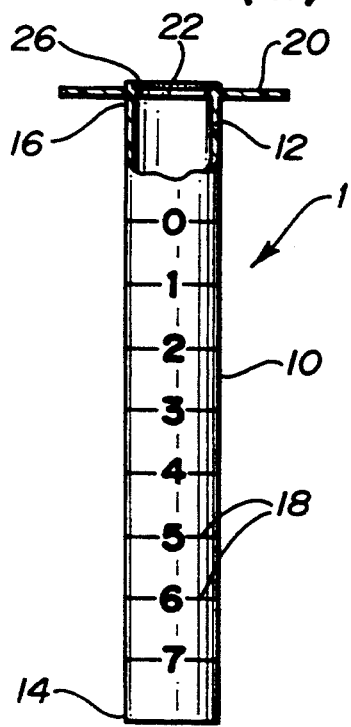
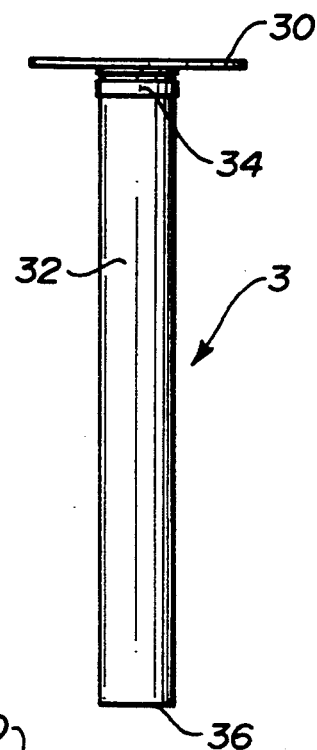
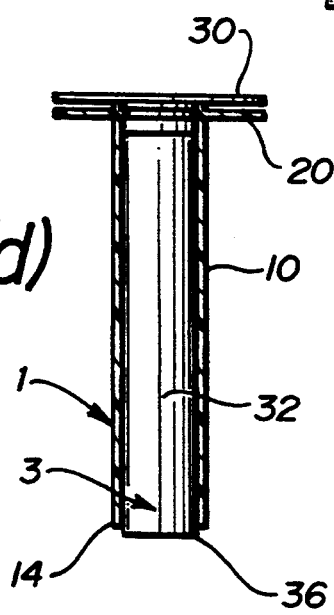
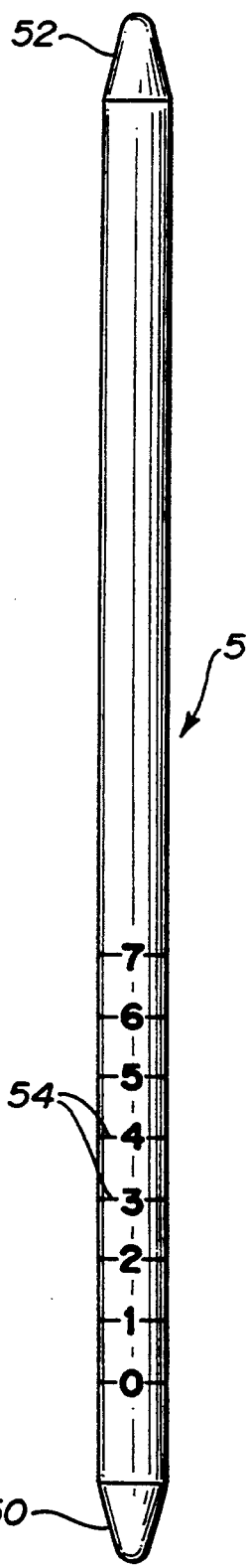

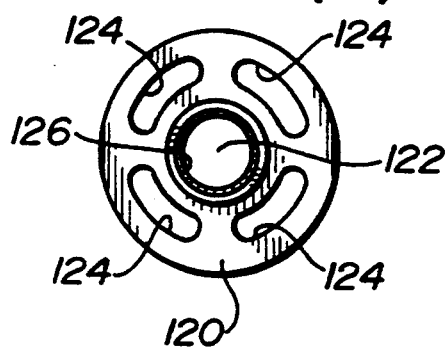
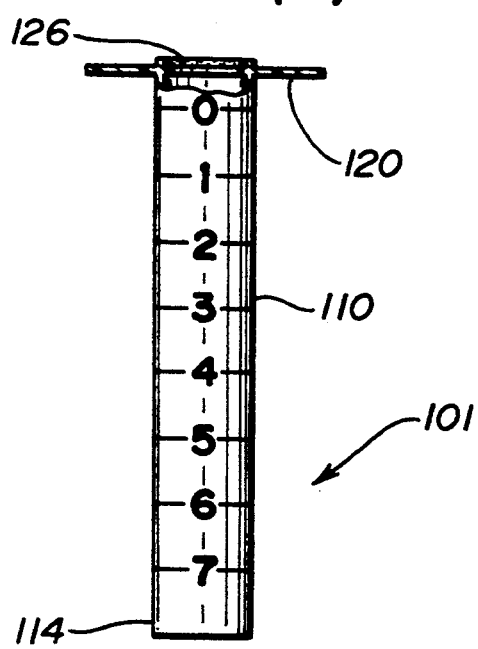
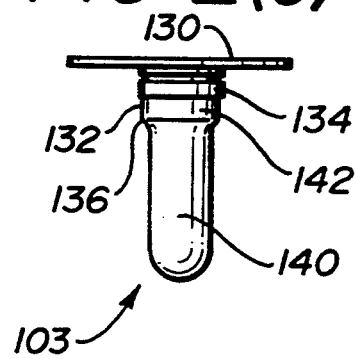
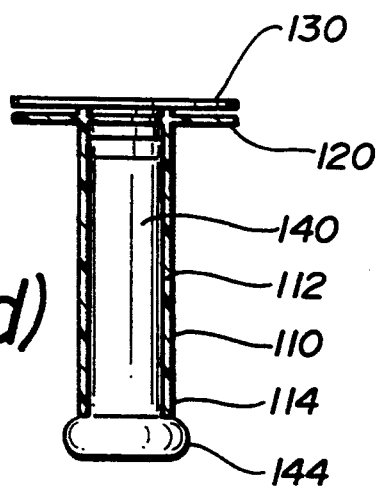

ENDOSCOPIC CLOSURE INSPECTION DEVICE

PRIORITY DATE

This patent application claims priority from DE P 42 29 873.3-35, filed Sep. 4, 1992.

FIELD OF THE INVENTION

The invention relates to an endoscopic closure inspection device.

BACKGROUND OF THE INVENTION

In endoscopic operation techniques, and thus in laparoscopy, cannulae (trocar sleeves) are inserted with the help of trocar obturators into the abdominal wall, in order to make the abdominal area accessible to endoscopic instruments. The operational field can be viewed and the operation itself performed by means of such instruments, observation optics, gripping instruments, cutting instruments, etc. The traumatic effects induced by a trocar are slight compared with those caused by conventional incisions. Such operation techniques generally mean that the patient has a shorter hospital stay, heals more rapidly and enjoys a better cosmetic outcome. For instance, laparoscopic cholecystectomy has thus now gained wide acceptance.

As with all surgical manoeuvres, complications occasionally occur with the endoscopic techniques, e.g., infections, internal bleeding, etc. In the case of laparoscopic cholecystectomy, the complications rate is of the order of magnitude of 5% or less. In many such cases, the patient must undergo another operation, which can negate the advantages of the endoscopic technique, for instance if an open abdominal surgery operation is necessary.

SUMMARY OF THE INVENTION

An object of the invention is to provide the possibility of keeping an operation area monitorable and accessible, even after a laparoscopic operation, in a manner which is considerate of the patient's condition.

This object is achieved by an endoscopic closure inspection device which contains a guide device for preventing a trocar puncture from healing and thereby closing, and a closure device through which the guide device is closeable. The guide device replaces a conventional cannula and prevents the puncture caused by the trocar from closing or growing together. If a conventional cannula were left within the puncture, this would be very uncomfortable for the patient and unacceptable medically, because such a cannula has a comparatively voluminous handle, which could be incorporated into a sterile dressing only with difficulty. The conventional cannula is stiff and long, a fact which may possibly lead to internal organ damage, and patient pain.

In contrast, the guide device disclosed herein is closeable by a closure device which preferably fills the guide device completely. This prevents pathogens from entering the inside of the body and, if the closure device completely fills the guide device, prevents organ parts from creeping into the distal end of the guide device. For monitoring of the operation area after the operation, the guide device can be used to guide endoscopic instruments, suction or lavage devices into the inside of the body again, or it can serve to guide a conventional cannula through the puncture point again. This is less stressful for the patient than if a fresh insertion is made with the help of a trocar. This method is also much safer, as no sharp trocar is needed to insert the cannula. It is thus not only conceivable to open the endoscopic inspection device in order to make the operation area accessible during later complications, but it could also be used routinely to recognize complications at an early stage, and thus lessen their effects.

In an advantageous version, the guide device comprises a sleeve with a flange at its proximal end. The sleeve is preferably trimmable at its distal end to a length somewhat exceeding the tissue thickness at the place of use. The guide reliably prevents the puncture from growing together, but its overall length does not substantially exceed the thickness of the abdominal wall, which is much more pleasant to the patient. The dimensions of the sleeve preferably correspond to those of a standard cannula, so that on the one hand it can be used easily and, where appropriate, exchanged for a standard cannula, and on the other hand permit the use of an endoscopic instrument which fits within the sleeve. In an alterative design, the sleeve can also have an internal diameter which is somewhat greater than the external diameter of a standard cannula; where appropriate, a standard cannula can then be guided through it.

The closure device preferably comprises a flange which is insertable within the flange of the guide device. The endoscopic closure inspection device then projects outwardly from the skin only slightly and can thus be readily incorporated under a sterile antiseptic dressing.

To prevent tissue, organs or organ parts from moving into the distal end of the sleeve, it is advisable for the closure device to be at least the same length as the sleeve, or to extend somewhat further into the inside of the body than the sleeve. This can be achieved by use of a stopper which extends through the sleeve and to whose proximal end the flange of the closure device is attached. Another possibility is to cover the aperture in the flange of the closure device, which aperture is located in the area of the sleeve, with a material which is self-sealing after having been pierced, e.g. latex, and apply on the side facing towards the sleeve an envelope which is made from expandable material and insertable into the sleeve. This envelope can be filled with a liquid or gaseous medium following insertion into the sleeve, so that it occupies the whole inside of the sleeve (and may also extend somewhat beyond the distal end of the sleeve). In this way there are no sharp-edged transitions in the inside of the body.

In another version, the guide device is a flexible tube whose external diameter is slightly smaller than the internal diameter of a standard cannula. The tube is preferably closed at its distal end by a balloon which is expandable by means of a liquid or gaseous medium. The combination of tube and balloon serves both as a guide, and as a closure device. At the end of the operation, the tube is guided with the deflated balloon through a conventional cannula used during the operation and then inflated with a gaseous or liquid medium. The balloon expands below the distal end of the cannula. The cannula can then be removed, and is guided along the guide device. The tube is now drawn outward until the expanded balloon lies against the puncture point in the inside of the body. On the outside, the tube can be folded against the abdomen and covered with an antiseptic dressing. If the operational field is to be observed or made accessible, the tube facilitates the introduction of a conventional cannula. When the balloon deflates, the tube can be removed.

The invention also relates to an endoscopic closure inspection system which comprises an inspection closure with a sleeve which is in the form of a hollow cylinder open at both ends, and an essentially cylindrical guide rod, the diameter of the latter being smaller or only slightly smaller than the internal diameter of a standard cannula, and its length exceeding the length of the sleeve. The guide rod and the sleeve are preferably provided with a measurement scale. The guide rod facilitates the insertion of the sleeve. With the help of the measurement scale on the guide rod, the thickness of the tissue layer can be measured in order to trim the sleeve to afford insertion of the closure device.

DESCRIPTION OF THE DRAWINGS

The invention is described more precisely below with reference to embodiments. The drawings show:

A first embodiment for an endoscopic inspection closure according to the invention, with FIG. 1(a) offering a side view, partly represented as a longitudinal section, of the guide device; FIG. 1(b) a top view of the guide device looking in distal direction; FIG. 1(c) a side view of the closure device designed as a stopper; FIG. 1(d) a side view, partly represented as a longitudinal section, of the stopper inserted in the guide device, both parts being trimmed to the desired size; and FIG. 1(e) a side view of guide rod;

A second embodiment for an endoscopic inspection closure according to the invention, with FIG. 2(a) offering a side view, partly represented as a longitudinal section, of the guide device; FIG. 2(b) a top view of the guide device looking in distal direction; FIG. 2(c) the closure device, designed as a blank flange fitted with an expandable envelope; in side view and FIG. 2(d) a side view, partly represented as a longitudinal section, of the closure device inserted into the trimmed guide device; and A third embodiment for an endoscopic inspection closure according to the invention, FIGS. 3(a) to 3(f) representing the individual steps for the introduction and removal of the endoscopic inspection closure designed as a tube with an expandable balloon.

DETAILED DESCRIPTION OF THE INVENTION

Figure 3A:
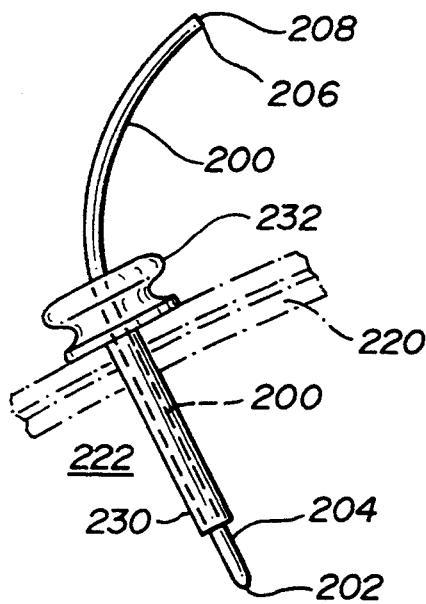
Figure 3B:
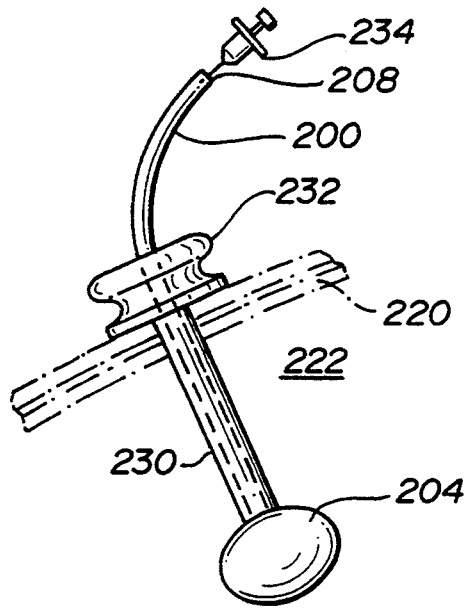

FIG. 1 shows an endoscopic closure inspection system with an endoscopic closure inspection device according to the invention, the latter comprising a guide device 1 and a closure device 3, the inspection closure system also having a guide rod 5.

The guide device 1 contains a sleeve 10 which essentially has the form of a hollow cylinder with a wall 12, distal end 14 and proximal end 16 being open. The internal diameter and the external diameter of the sleeve 10 are preferably the same as the corresponding dimensions of a standard trocar cannula; in another version, the internal diameter of the sleeve 10 is slightly greater than the external diameter of a standard cannula. The outside of the sleeve 10 can be provided with a measurement scale 18.

At its proximal end 16, a flange 20 is secured to the sleeve 10. The flange 20 can assume all possible forms; here it is of annular design with an aperture 22 in the area of the sleeve 10. Between its inside and outside edges it is provided with several openings 24. A sealing ring 26 is arranged about the aperture 22.

The sealing ring 26 acts as a germ barrier. To this end, it is preferably provided with a germicide. The guide device 1 and closure device 3 can be sealed off from each other via the sealing ring 26. (Sterile conditions are important for the success of the operation. The sealing ring 26 helps ensure these by guarding the inside of the sleeve 10 against infection germs. Such germs cannot, accordingly, be spread into the operation area, e.g., via endoscopic instruments or cannulae subsequently introduced into the sleeve 10.)

The closure device 3 comprises a flange 30 to which a stopper 32 is secured. The flange 30 is matched to the flange 20 of the guide device 1; the external diameters agree and openings of the flange 30 (not shown) corresponding to the openings 24. The stopper 32 is cylindrical and its external diameter is slightly smaller than the internal diameter of the sleeve 10. In the vicinity of the flange 30, the stopper 32 can be provided with a sealing surface 34. When in use, it is advantageous if the distal end 36 of the stopper 32 either ends with the distal end 14 of the sleeve 10 or projects further into the inside of the body, see FIG. 1(d).

The guide device 1 and the closure device 3 can be made from a material suitable for medical purposes. In particular, it is advantageous if the sleeve 10 and the stopper 32 are made from flexible or solid plastics materials, as they can then be easily trimmed at a desired point during the operation so as to match them to the tissue thickness of the patient. This will be described in more detail below. It is also conceivable to produce the sleeve 10 and the stopper 32 in various standard lengths, the surgeon choosing the correct length according to the patient's general features.

FIG. 1(e) shows the guide rod or dilator 5, which serves to determine the necessary length of sleeve 10 and stopper 32 and to remove the cannula used during the operation and fit the sleeve 10 within a puncture site, as will be described below. The guide rod 5 is essentially cylindrical, its diameter being slightly smaller than the internal diameter of a (standard) cannula (anywhere between 3 mm and 33 mm diameter) and its length exceeding the length of the sleeve 10. The guide rod 5 is preferably rounded at its distal end 50 and at its proximal end 52. If used to measure the necessary sleeve length, it is provided with a measurement scale 54 in its distal zone. The "0" mark is somewhat offset with respect to the distal end 50.

The first embodiment of the endoscopic inspection system can be used as follows. Towards the end of the operation, the surgeon decides that the conventional cannula used during the operation is to be replaced by the endoscopic inspection device according to the invention. After removal of the operation instruments from this cannula, the guide rod 5 is introduced, under constant observation via an endoscopic optical device. The cannula can then be drawn out along the guide rod from the puncture site. The guide rod 5 prevents the closure of the wound. Under endoscopic observation, the "0" mark of the guide rod 5 is now brought against the inside of the penetrated tissue layer. The pointed indicated as "0" is offset with respect to the distal end 50 for the purpose of keeping the incision apart inside the body. The thickness of the penetrated tissue layer can be read off on the measurement scale 54. The sleeve 10 is trimmed according to the numerical value which is read, preferably together with the inserted stopper 32. Since the "0" mark is offset with respect to the proximal end 16, the distal end 14 projects somewhat further into the inside of the body after the sleeve 10 has been inserted into the tissue layer, so that the margin of tissue incision cannot slip over the distal end 14 of the sleeve 10.

The sleeve 10 is then inserted into the incision via the guide rod 5 until the flange 20 lies against the skin. The guide rod 5 is then withdrawn. The closure device 3 can now be inserted in to the guide device 1. It is advisable to secure the flange 20 at the skin so that it does not slip out. For example, flange 20 can be secured by: sticking it on with a double-sided adhesive tape (one adhesive surface lying against the underside of the flange 20 and the other against the skin); sticking it on firmly with a plaster; or by sewing. When sewing at the skin, the openings 24 are useful. It is also conceivable to secure the closure device 3 at the guide device 1, e.g. via screws or with the help of a thread at the shaft of the stopper 32 which engages in a corresponding counter-thread at the sleeve 10 (not shown). Finally, flanges 20 and 30 are covered with a sterile antiseptic dressing.

As the endoscopic inspection closure according to the invention has no parts projecting either well outward or well into the inside of the body, there is no discomfort for the patient, yet the system reliably prevents the puncture site from growing together or closing. If no complications have arisen after some time, the sleeve 10 can easily be withdrawn from the puncture point. In the case of complications or also for routine monitoring, the sleeve 10 can be used. After the closure device 3 is removed, endoscopic instruments can be introduced into the inside of the body or even, if the interior dimensions of the sleeve 10 allow, a standard trocar cannula can be fitted into the sleeve 10. Where appropriate, a top piece can be fitted onto the flange 20 and secured by suitable means, this top piece being provided with a sealing flap and compressed-gas valve, similar to the system used for conventional cannulae.

FIG. 2 shows a second embodiment for an endoscopic inspection closure according to the invention. The inspection closure comprises a guide device 101 and a closure device 103 and is supplemented where appropriate by a guide rod, not shown, to complete the system. The guide device 101 is essentially structured like the guide device 1 from the previous embodiment. It comprises a cylindrical sleeve 110, the dimensions of which are matched to a conventional cannula, with a flange 120. The flange 120 has an aperture 122, openings 124 and a sealing ring 126. The closure device 103 contains a blank flange 130 which is matched to the flange 120 of the guide device 101. Provided at the blank flange 130 in the area of the sleeve 110 is an aperture which is preferably covered by a material which automatically closes up again after being pierced. Latex is an example of such a material. Close to the edge, the blank flange 130 can have openings which correspond to the openings 124. On the side facing towards the flange 120 in the assembled state, a socket 132 in the form of a cylindrical jacket is secured at the blank flange 130. If required, the socket 132 can have a sealing surface 134 at its outside.

In the vicinity of its distal end 136, the proximal zone 142 of an envelope 140 is attached to the socket 132. The envelope 140 consists of an expandable material. The envelope 140 can be filled with a liquid or gaseous medium via the closeable aperture provided in the blank flange 130 when the closure device 103 is inserted into the guide device 101. Examples of suitable media of this kind are physiologically compatible saline solution or carbon dioxide. Upon filling, the envelope 140 expands until its distal zone 144 protrudes relative to the distal end 114 of the sleeve 110, as shown in FIG. 2(d). This avoids the presence in the inside of the body of any sharp edges which could lead to complications in the intra-abdominal area. The envelope 140 also lies tight against the inside of the wall 112 of the sleeve 110, so that a sealing effect is achieved in this way.

The use of the inventive endoscopic inspection closure as per the second embodiment is similar to that in the case of the first embodiment. Instead of the closure device 3, however, the closure device 103 consisting of the blank flange 130 and the envelope 140 are to be inserted into the sleeve 110 in order to close the inspection closure. The envelope 140 is then filled with a liquid or gaseous medium until its distal zone 114 emerges at the distal end 114 of the sleeve 110. If the aperture in the blank flange 130 is covered by a self-sealing material, filling can take place with the help of a syringe. Following withdrawal of the injection cannula, the aperture then closes automatically and the medium with which it has been filled cannot escape.

Alternatively, the aperture in the blank flange 130 can also be fitted with a valve. In order to remove the closure device 103 from the sleeve 110, the medium must be sucked out first, again possibly with the help of a syringe where appropriate. The blank flange 130 can then be easily removed with the slackened envelope 140.

In the case of the embodiment shown in FIG. 3, the guide device comprises a flexible tube 200. The external diameter of the tube 200 is slightly smaller than the internal diameter of a standard cannula. At is distal end 202, the tube 200 is closed by a balloon 204. In a deflated condition the balloon 204 can be pushed through a conventional cannula just as easily as can the tube 200. The balloon 204 can be made separately and tightly secured at the distal end 202 of the tube 200. However, it can also be make in one piece with the tube 200, displaying a lesser wall thickness than the tube 200. If the tube 200 is filled from its proximal end 206 with a liquid or gaseous medium, e.g. with saline solution or carbon dioxide, the balloon expands markedly, see e.g., FIG. 3(b). At its proximal end 206 the tube 200 contains a closure 208. This can be for example a layer which is tightly secured at the tube 200 and made from a material which is self-sealing after being pierced, such as latex. A tube clamp or a valve are also conceivable.

Figure 3C:
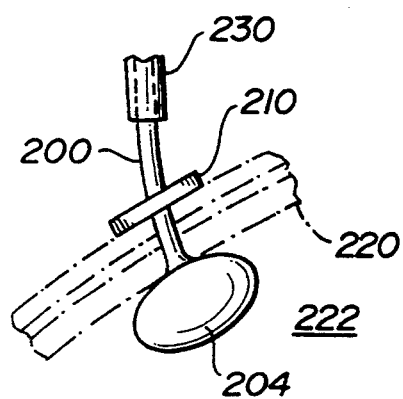
Figure 3D:
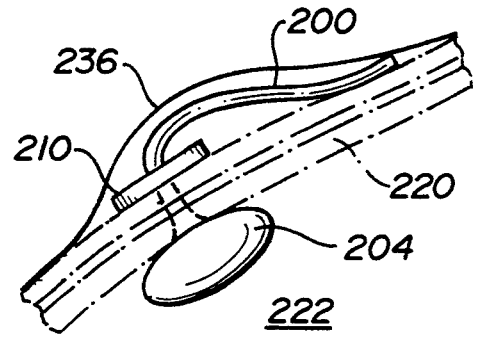

The endoscopic closure inspection system according to this embodiment can also contain, as an additional element, a plate 210, see FIGS. 3(c) and 3(d). The plate 210 has a centrally located aperture through which the tube 200 fits, sealing against the aperture when appropriate. A clamping device for the tube 200 is preferably attached to the plate 210. On its distal side, the plate 210 can be provided with a seal lying against the skin. The details of the plate 210 are not illustrated in FIG. 3.

FIG. 3 shows the individual steps in the application of the inventive endoscopic inspection closure in accordance with the third embodiment.

In FIG. 3(a), a cannula 230 which bears a top piece 232 (e.g. with a valve flap and a compressed-air valve) is introduced into the abdominal area 222 through the multi-layered abdominal wall. This situation exists during any endoscopic operation. To introduce the endoscopic closure inspection system, the tube 200 is now pushed through he cannula 230 under endoscopic observation until its distal end 202 with balloon 204 projects into the abdominal area.

As a next step, a syringe 234 which penetrates the closure 208 at the end of the tube 200 is used to fill the tube 200 with a liquid or gaseous medium. (See FIG. 3(b).) Under the pressure of this medium, the balloon 204 expands in the abdominal area, while the tube 200 negligibly changes diameter. After the syringe 234 has been withdrawn, the closure 208 seals automatically.

As shown in FIG. 3(c), the cannula 230 can then be removed from the puncture site and the tube 200 moved outward until the inflated balloon 204 lies against the interior of the incision. Closing of the wound is prevented, but in a particularly gentle manner. To safeguard the tube 200 against slipping, the plate 210 can be clamped about the tube 200 on the outside of the puncture point. If the plate 210 is provided with a seal on the side facing the skin, a sealing effect is also achieved.

FIG. 3(d) shows the situation of the endoscopic inspection closure once introduction is complete. The tube 200 is laid against the skin and, just like the plate 210, is covered by a sterile antiseptic dressing 236.

Figure 3E:
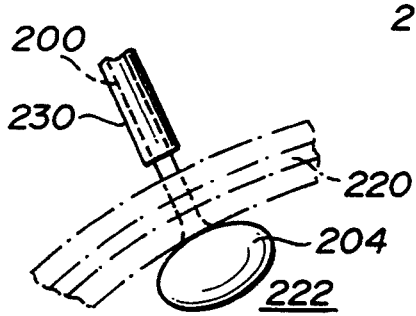

If the operational area is to be observed again or made accessible to endoscopic instruments, it is necessary to introduce a cannula 230, which is guided with the help of the tube 200. FIG. 3(e) illustrates this process shortly before the distal end of the cannula 230 touches the skin.

Figure 3F:
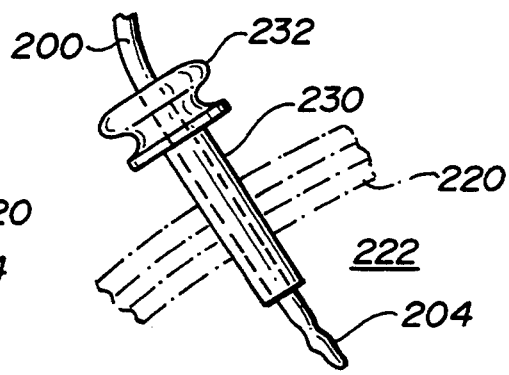

To prevent the cannula 230 from destroying the balloon 204 and the medium with which the balloon 204 has been filled from contaminating the abdominal area 222, the balloon 204 must be deflated prior to the insertion of the cannula 230, as shown in FIG. 3(f).

If an endoscopic inspection closure is to be inserted repeatedly at the same puncture point, for reasons of sterility a new tube 200 is necessary every time. On the other hand, endoscopic inspection closure as per the first embodiment can be used several times.

In addition to the embodiments described in detail, many other versions are conceivable for an endoscopic inspection closure according to the invention. For example, a cannula used during the actual operation could be fitted with a sleeve cap which is structured as a guide device for an endoscopic inspection closure in a similar manner to the first or second embodiment. In this case it would not be necessary to remove the cannula completely and then insert the guide device. The same effect can be achieved if a sleeve serving as a guide device of an inspection closure is designed as an outer sleeve of the cannula used during the actual operation. Alternatively, an endoscopic closure inspection according to the invention and similar to the first or second embodiments could be introduced with the help of a cannula and specifically used for inspection and monitoring purposes.

What is claimed is:

1. Endoscopic closure inspection device comprising:
   a guide device for long term placement into the body, said guide device comprising a sleeve having an internal diameter and a length with a flange at its proximal end and a cylindrical guide rod emplaceable into said sleeve, said guide rod having an outer diameter less than the internal diameter of said sleeve and a length longer than the length of said sleeve; said guiding device inserted into a puncture site in the body and said guiding device preventing said puncture site from healing; and
   a closure device which is insertable into said sleeve.

2. Endoscopic inspection device according to claim 1 characterized in that the sleeve is made from plastic.

3. Endoscopic inspection device according to claim 1 characterized in that the flange is provided with spaced apart openings.

4. Endoscopic inspection device according to claim 2, characterized in that the flange has a patient facing underside with a double-sided adhesive tape on said underside.

5. Endoscopic inspection device according to claim 1 characterized in that a germ barrier is arranged at the flange.

6. Endoscopic inspection device according to claim 5 characterized in that the germ barrier is a sealing ring on the side of the flange facing away from the sleeve.

7. Endoscopic inspection device according to claim 1 characterized in that an aperture is provided in the flange in the area of the sleeve and is covered with a material which seals itself after being pierced.

8. Endoscopic inspection device according to claim 1 characterized in that the closure device has a stopper provided with a flange which abuts the flange of the guide device when said closure device is inserted into said sleeve.

9. Endoscopic inspection device according to claim 8 characterized in that the stopper projects slightly beyond the distal end of the sleeve.

10. Endoscopic inspection device according to claim 9 characterized in that the stopper consists of plastic material.

11. Endoscopic closure inspection device comprising:
    a guide device for long term placement into the body, said guide device comprising a sleeve having an internal diameter and a length with a flange at its proximal end;
    said guiding device inserted into a puncture site in the body and said guiding device preventing said puncture site from healing; and
    a closure device which is insertable into said sleeve closure device having, on the side of the flange facing the guide device, an envelope closed by the flange, said envelope made from expandable material.

12. Endoscopic inspection device according to claim 11 characterized in that the envelope can be extended beyond the distal end of the sleeve.

* * * * *